United States Patent [19]
Lawrence et al.

[11] Patent Number: 5,516,671
[45] Date of Patent: May 14, 1996

[54] METHOD OF CONTROLLING PLANT PATHOGENS

[75] Inventors: Ellen B. Lawrence, Creve Coeur; Elaine B. Levine, St. Louis; Dilip M. Shah, Chesterfield, all of Mo.

[73] Assignee: Monsanto Company, St. Louis, Mo.

[21] Appl. No.: 333,802

[22] Filed: Nov. 3, 1994

Related U.S. Application Data

[63] Continuation-in-part of Ser. No. 161,041, Nov. 24, 1993, abandoned.

[51] Int. Cl.$^6$ .................. A01H 1/04; C07H 17/00; C12N 15/00; C12N 5/14
[52] U.S. Cl. ............ 435/172.3; 435/69.1; 435/70.1; 800/205; 800/DIG. 42; 536/23.2; 536/23.7
[58] Field of Search .................. 800/205, DIG. 42; 435/69.1, 70.1, 172.3, 240.49, 320.1; 536/23.2, 24.1, 23.7

[56] References Cited

U.S. PATENT DOCUMENTS

| | | | |
|---|---|---|---|
| 4,696,674 | 9/1987 | Cipar | 800/200 |
| 4,723,052 | 2/1988 | Cochran | 800/200 |
| 4,940,840 | 7/1990 | Suslow | 800/205 |
| 5,266,688 | 11/1993 | Rosenberg | 536/23.2 |
| 5,270,194 | 12/1993 | D'Alterio et al. | 435/188 |

FOREIGN PATENT DOCUMENTS

WO89/12675 12/1989 WIPO.

OTHER PUBLICATIONS

Kim et al., Identification of a Metabolite Produced by *Talaromyces flavus* as Glucose Oxidase and its Role in the Biocontrol of *Verticillium dahliae*. Phytopathology 78:488–492, 1988.

Kim et al., Production, purification, and properties of glucose oxidase from the biocontrol fungus *Talaromyces flavus*. Can. J. Microbiol. 36:199–205 1990.

Koster–Topfer et al., A Class II Patatin Promoter Is under Developmental Control in Both Transgenic Potato and Tobacco Plants. Mol. Gen. Genet 219:390–396, 1989.

Kriechbaum et al., Cloning and DNA Sequence Analysis of the Glucose Oxidase Gene from *Aspergillus niger* NRRL–3. FEBS Lett. 225(1):63–66, 1989.

*Primary Examiner*—David T. Fox
*Assistant Examiner*—Elizabeth F. McElwain
*Attorney, Agent, or Firm*—Grace L. Bonner; Dennis R. Hoerner, Jr.; Richard H. Shear

[57] ABSTRACT

Plants can be transformed to express glucose oxidase from *Aspergillus sp.* and be made resistant to bacterial and fungal pathogens. Optionally, the plants may also express invertase to increase the available glucose as a substrate for enzymatic activity.

13 Claims, No Drawings

METHOD OF CONTROLLING PLANT PATHOGENS

This application is a continuation-in-part of U.S. Ser. No. 161,041, filed Nov. 24, 1993, now abandoned.

FIELD OF THE INVENTION

This invention relates to a method of controlling plant pathogens by a protein which is provided by genetically modifying the plant to produce the protein, and to genes and plants useful in that method.

BACKGROUND OF THE INVENTION

It is well known that the enzymatic action of glucose oxidase is antibacterial. In the presence of oxygen, glucose oxidase catalyzes the oxidation of glucose to ∂-gluconolactone and hydrogen peroxide. The antibacterial mode of action is due to both the oxidative potential of hydrogen peroxide as well as the presence of the ∂-gluconolactone, which is a known glycosyltransferase inhibitor.

The antibacterial effect of the products of this enzyme has resulted in its wide-spread use in the food industry, where it is considered a GRAS [generally recognized as safe] compound. As such, glucose oxidase is used to prevent bacterial spoilage of prepared foods. In medicine, it is used as an enzymatic bactericide as part of a preparation for use in wound dressings, toothpicks, dental floss and miniature tooth-brushes. Glucose oxidase has also been mentioned as a method to control dental caries.

Recent reports have shown that a glucose oxidase is involved as part of the bio-control mechanism used by *Penicillium dangearii* to control the plant pathogenic fungus *Verticillium dahliae*. [Kim et al., 1988, 1990].

However, the use of glucose oxidase as a means for plants to protect themselves from pathogenic organisms has been thought to have little potential due to the nature of the enzymatic action. First, there is little free glucose present in plants. The enzyme would seem to have insufficient substrate to produce enough hydrogen peroxide and/or ∂-gluconolactone to overcome a pathogenic attack. Second, the presence of such an enzyme in a plant cell, consuming glucose and producing even a small amount of hydrogen peroxide, would be expected to be detrimental to the vitality of the cell. Transgenic plants expressing glucose oxidase would not be expected to develop normally, either as regenerated plants or in subsequent generations.

It is an object of the present invention to provide a glucose oxidase that can be safely expressed in plant cells and provide disease resistance to those cells. It is a further object of the present invention to provide a method of transforming plants to express a glucose oxidase which can be safely expressed in plants and provide disease resistance to those plants.

SUMMARY OF THE INVENTION

Surprisingly, it has been found that the gene for glucose oxidase from *Aspergillus niger* can be used to transform plants, which are developmentally normal and resist pathogenic attack. It is, therefore, an object of the present invention to provide genetic constructs comprising a gene for Aspergillus glucose oxidase (AGO) useful for insertion into plant cells. It is another object of the present invention to provide transformed, pathogen-resistant plants containing such genetic material.

Additionally, the plants may also be transformed to co-express other anti-fungal proteins or insecticidal proteins, for example, using *Bacillus thuringiensis* (B.t.) genes. Examples of plants transformed to express B.t. genes are disclosed in European Patent Publication No. 0 385 962, which corresponds to U.S. Ser. No. 07/476,661, filed Feb. 12, 1990 [Fischhoff et al.], which is incorporated herein by reference. A B.t. gene may be incorporated into a plant of the present invention by simultaneous transformation, sequential transformation, or by breeding.

In accordance with an aspect of the present invention, there is provided a recombinant, double-stranded DNA molecule comprising in operative sequence:
  a) a promoter which functions in plant cells to cause the production of an RNA sequence; and
  b) a structural coding sequence that codes for production of AGO;
  c) a 3' non-translated region which functions in plant cells to cause the addition of polyadenylate nucleotides to the 3' end of the RNA sequence. In accordance with another aspect of the present invention, there is provided a method of producing genetically transformed plants which express an antipathogenic amount of AGO, comprising the steps of:
  a) inserting into the genome of a plant cell a recombinant, double-stranded DNA molecule comprising
    (i) a promoter which functions in plant cells to cause the production of an RNA sequence;
    (ii) a structural coding sequence that codes for production of AGO;
    (iii) a 3' non-translated region which functions in said plant cells to cause the addition of polyadenylate nucleotides to the 3' end of the RNA sequence;
  b) obtaining transformed plant cells; and
  c) regenerating from the transformed plant cells genetically transformed plants which express an inhibitory amount of AGO.

There is also provided, in accordance with another aspect of the present invention, transformed plants that contain DNA comprised of the above-mentioned elements (i), (ii), and (iii).

As used herein, the term "Aspergillus glucose oxidase" or "AGO" is used to indicate a glucose oxidase naturally produced by Aspergillus sp. or having >80% homology, preferably >90%, to such an enzyme, for example, the enzyme encoded by SEQ ID NO: 1.

As used herein, the term "controlling microbial damage" or "pathogen-resistance" is used to indicate causing a reduction in damage to a crop due to infection by a bacterial or fungal pathogen.

As used herein, the term "structural coding sequence" means a DNA sequence which encodes for a polypeptide, which may be made by a cell following transcription of the DNA to mRNA, followed by translation to the desired polypeptide.

As used herein, the term "plant locus" means the area immediately surrounding a plant and including the plant and its root zone.

DETAILED DESCRIPTION OF THE INVENTION

One embodiment of the present invention comprises a protein isolated from *Aspergillus niger*. This protein, designated AGO, has been purified to homogeneity. It inhibits the growth of the agronomically important fungal pathogens, including, *Verticillium dahliae*, one of the most widespread and damaging plant pathogens, causing disease in many plants, *Phytophthora infestans* (Pi), the causal pathogen of late blight disease in potato and tomato, *Botrytis cinerea* (Bc), the source of gray mold on various fruits and vegetables, *Septoria nodorum* (Sn), the causal agent of wheat glume blotch, *Pseudocercosporella herpotrichoides* (Ph), the causal agent of wheat eyespot, and *Gaeumannomyces graminis* var tritici (Ggt), the causal agent of Take-all disease in cereals, with an amount as little as 50 ng under the assay conditions. It has also been found to inhibit *Erwinia carotovora*, the causal agent of potato soft rot, a post-harvest disease of potatoes. It is expected to be capable of controlling many other plant pathogenic organisms based on the products of its enzymatic activity, ∂-gluconolactone and hydrogen peroxide. Each of these by-products is toxic to such organisms.

Many species of plants may be protected by the methods of the present invention. For example, many fruits and vegetables such as strawberries, potatoes, and tomatoes may be protected from plant pathogens by the present methods. Various Phytophthora species are pathogenic to many other plants, such as fruit trees or turf, and thus these plants may also be protected by the methods of the present invention. Furthermore, wheat and barley plants may be protected from Ggt, Sn, and Ph, by the present method.

As noted above, the antimicrobial proteins of the present invention may be used in combination with other antifungal proteins so as to provide a broad spectrum of activity, i.e., control additional pathogens, and/or provide multiple modes of action for the inhibition of the same fungal pathogen. Sources of such other antifungal proteins might be microbial, such as the proteins of the present invention, or may be plants. Many such antifungal genes are reported in the literature.

Although AGO will function to protect plants from pathogenic attack in the presence of naturally occurring levels of glucose, it may be desirable to provide an invertase which will cause the hydrolysis of sucrose, thus releasing additional glucose for the AGO to act on. The invertase will preferably be a cell wall invertase such as from yeast (EP 0 442 592, Willmitzer et al., 1991, also AU 70898/91) or a vacuolar enzyme such as from tomato or other plants. In these two cases the native signal sequences may be used; however, it may be preferable that the invertase be sequestered until needed in the extracellular space, or not produced until needed. The first alternative may be accomplished by the use of a signal sequence which will direct the enzyme to the extracellular space. One such signal is the potato protease inhibitor signal (Keil et al., 1986; Nelson et al., 1980). A promoter that is only active as a result of a pathogenic infection would be useful in limiting the expression of invertase to when it is actually needed to produce glucose as a substrate for AGO.

During storage, when Erwinia infection can cause the loss of a whole bin, potato tubers will naturally contain glucose from the breakdown of starch. Therefore, inclusion of a gene for invertase is not desired or necessary for protection from soft rot.

IN VITRO BIOEFFICACY ASSAYS

Antifungal assays

Glucose oxidase from *Aspergillus niger* can be obtained from Sigma Chemical Co. (St. Louis, Cat.# G-7141). It was used to test the in vitro activity against several organisms.

Tests against Pi and Bc were conducted in Medium #303, prepared as follows: One liter contains 1 g $MgSO_4.7H_2O$; 2 g $KH_2PO_4$; 0.5 g NaCl; 1 g $CaCO_3$; 1 ml $ZnSO_4.7H_2O$ stock—1 mg/ml; 1 ml $FeSO_4.7H_2O$ stock—1 mg/ml; 0.5 ml FeEDTA stock—100 mM; 20 g Maltrin M-100; 20 g Casein; 5 g Yeast Extract; 5 g Glucose; 3.02 g Pipes 10 mM; pH adjusted to 6.5 and filter sterilized. Tests against Ggt were conducted in half-strength PDA (Difco). Tests against Ph were conducted in CDAA 0.1% media prepared as follows: 35 g/l Difco Czapek Dox Broth, 1 g/l Proline, 500 mg/l Asparagine, 500 mg/l Cysteine, and 1 g/l Agar are autoclaved for 23 minutes, and filter-sterilized vitamins (1 ppm Thiamine and 1 ppm Biotin) are added.

Bc and Pi were tested in a liquid assay in 96-well plates. Bc was used at $5 \times 10^2$ spores per well and allowed to incubate at 20° C. for 24–48 hours. Pi is seeded at $5 \times 10^3$ sporangia per well and allowed to incubate at 18° C. for 24–48 hours. Assessment of growth is made by measuring the OD at 595 nm. The growth of Pi was 90% inhibited at concentrations as low as $3 \times 10^{-5}$ IU/µl. The growth of Bc was 95% inhibited at 0.001 IU/µl.

Activity against Gaeumannomyces was evaluated on solid agar plates. An approximately 0.5 $cm^2$ piece of agar supporting heavy fungal growth was placed in the center of a half-strength PDA plate and allowed to grow out for several days at 22° C. At 1 cm beyond the leading edge of growth a 0.5 cm diameter plug of agar was removed aseptically with a sterile cork borer. Sterile AGO stock was added directly to these wells. A visible zone of inhibition was apparent with amounts as low as 0.02 IU/well.

Tests against Ph were conducted in 96-well plates. A 14 day old culture of *Pseudocercosporella herpotrichoides* var. tritici on water agar is used to make the spore suspension. A plate is flooded with 5–10 ml of CDAA 0.1% media and spores are mixed into the liquid media by swirling gently. The concentrated spore suspension is drawn off with pipet and added to the total volume of CDAA required for the test, adjusting spore concentration to 100,000 spores/ml. Assay incubation is at 24° C. in darkness.

The spore suspension is dispensed at 50 µl/well in a 96 well microtiter plate. These plates are then placed in an incubator (10 hr/day light at 12° C.) for 24 hours prior to sample application. 50 µl of sample is added to the 50 µl of inoculum (prepared 24 hours earlier) resulting in a total well volume of 100 µl/treated well/replicate treatment. Assay plates are incubated for 48 hours and the results are determined by reading optical density (OD) with a BioRad microtiter plate reader model 3550 at a single wavelength of 595 nm. An OD reading is made at time zero ($t_0$) which is made immediately after sample application, and an OD reading is made at 48 hours after sample application ($t_{48}$). Fungal growth estimate is determined by the difference in OD readings between $t_0$ and $t_{48}$ multiplied by a calculation value for fungal biomass. (The calculation value for fungal biomass is the relationship between fungal growth and optical density and was determined in separate experiments. The relationship between fungal growth and optical density was determined by growing fungi in 96 well microtiter plates, and harvesting the mycelium over time, at absorbance intervals of approximately 0.1 OD. The calculation value comes from the linear relationship between fungal biomass and OD for the specific fungus. It is the slope value obtained from the linear relationship. The calculation value for Ph is 4.91) Then % inhibition is determined from the difference between the biomass of the treatments and the biomass of the controls. AGO exhibited 60% inhibition of Ph at $1.7 \times 10^{-4}$ IU/µl.

Tests against Sn were conducted essentially like those for Ph except for the spore suspension preparation. A seven day old sporulating culture of *Septoria nodorum* on YMA agar is used to make the spore suspension. A small amount (<1 ml) of CDAA media is dropped onto an area of the culture with pink spore masses oozing from the pycnidia. The spores are mixed with the CDAA media by repeatedly drawing up and expelling them from the pipetter. The concentrated suspension is added to the total volume of CDAA required for the test, adjusting spore concentration to 50,000 spores/ml. The calculation value for Sn is 0.508. AGO exhibited 60% inhibition of Sn at $1.7 \times 10^{-4}$ IU/µl.

Bacterial Assay

Cultures of the bacteria *Erwinia carotovora* are maintained by streaking onto PDA plates and incubating at 24° C. in the dark. To prepare inoculum broth, a loop of actively growing bacteria (5–9 days old) is added to 50 ml of ¼ strength PD broth in a 125 ml Erlenmeyer flask. The flask is placed on a shaker incubator (130 rpm) at 24° C. in the dark. After 24 hr, the bacteria are pelleted, resuspended in sterile deionized water, and three or four 100 µl aliquots are each placed in wells of a 96-well microtiter plate for readings. The microplate reader is set at 595 nm, and the average optical density of the wells is determined. This absorbance (ABS=optical density) number is used in the following formula to calculate colony forming units (CFUs) contained in the broth.

$$CFU = (3 \times 10^6) + [(3 \times 10^8) \times ABS] + [(5 \times 10^8) ABS^2]$$

The broth is adjusted for use to $10^5$ CFU.

AGO completely controlled growth of *E. carotovora* at concentrations as low as $3 \times 10^{-5}$ IU/µl.

ENZYME IDENTIFICATION

A number of methods may be devised to detect the production of a protein in a heterologous system such as plant cells. Western blot techniques may be used to detect a protein immunologically, or enzymatic or biological assays may be used to detect activity of the protein.

Glucose Oxidase Enzymatic Assay

A modification of a continuous spectrophotometric assay (Frederick et al., 1990) was utilized to establish GO activity. *Aspergillus niger* GO (Sigma) was used as a positive control. The reaction mixture consisted of 20 µg/ml horseradish peroxidase (Sigma), 0.32 mM Triton X-100-stabilized o-dianisidine solution (Sigma), and 0.1M glucose in 75 mM sodium phosphate buffer (pH 5.0). To this was added 100 µl of various concentrations of *A. niger* GO for the control reactions or 100 µl of sample derived from a heterologous source. The assay was performed at room temperature and the increase in absorbance was monitored at 460 nm.

An alternate assay for glucose oxidase utilizing the reagent 4-amino-antipyrine (4-AAP) was optimized for use based on Gallo, 1981. The 5X 4-AAP reagent is prepared at 10 ml total volume with 0.68 g $KH_2PO_4$, 8.3 mg 4-AAP (0.82 mM), 25 µl Triton X-100, 0.0658 g crystalline phenol, and 1000 U Horseradish peroxidase, with the pH adjusted to 5.0 with KOH. The assay is conducted by mixing 200 µl of this 4-AAP reagent, 5 µl 1 mM FAD, 50 µl 1M glucose; and the test sample (up to 750 µl). The result is read at OD508.

Glucose Oxidase Biological Activity Assay

A plug of 4–6 day old Ggt fungus was transferred onto fresh one-quarter-strength potato dextrose agar (Difco) plates. The fungus was grown at 22° C. for four days or until the circle of growth was about 2.5 cm. Using a sterile cork borer, wells were made in agar at 1 cm outside the circle of growth and 100 µl of buffer or sample derived from a heterologous source was placed in the wells. The fungus was grown for 24 hr at room temperature and examined for inhibition of growth.

Immunological Detection of Glucose Oxidase

Polyclonal antibodies to glucose oxidase produced by *Aspergillus niger* are available commercially from many sources, for example, Rockland, Inc., Gilbertsville, Pa.

GENETIC TRANSFORMATION

Cloning of the AGO Gene

Total DNA was isolated from *Aspergillus niger* (ATCC 9029) and used as a template for PCR isolation of a glucose oxidase gene. PCR primers were based on the published sequence of the gene (Frederick et al; Kriechbaum et al.) and were designed to isolate the entire sequence of the gene including the signal sequence. In addition, in order to facilitate the incorporation of this gene into vectors appropriate for expression in heterologous bacterial, baculovirus or plant systems, the 5' PCR primer (SEQ ID NO:3) introduced XbaI and BglII restriction endonuclease sites upstream of the ATG start of translation of the gene. The 3' PCR primer (SEQ ID NO:4) introduced the BamHI and KpnI restriction endonuclease sites immediately after the stop codon. The PCR fragment produced was cloned into pUC118 as a XbaI/KpnI fragment to create pMON22514 and was completely sequenced. The sequence (SEQ ID NO:1) exactly matched that of the published sequence. SEQ ID NO:2 is the deduced corresponding amino acid sequence.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the Figwort Mosaic Virus (FMV) 35S promoter, and the light-inducible promoter from the small subunit of ribulose 1,5-bis-phosphate carboxylase (ssRUBISCO, a very abundant plant polypeptide). All of these promoters have been used to create various types of DNA constructs which have been expressed in plants. U.S. Pat. No. 5,034,322 (Fraley et al., 1991), herein incorporated by reference, discloses such uses.

There are promoters known which will limit expression to particular plant parts or in response to particular stimuli. For example, potato tuber specific promoters, such as the patatin promoters or the promoters for the large or small subunits of ADPglucose pyrophosphorylase, could be used to obtain expression primarily in the tuber and thus, in combination with AGO, provide resistance to attacks on the tuber, such as by Erwinia. A fruit specific promoter would be desirable to impart resistance to Botrytis in strawberries or grapes. A root specific promoter would be desirable to obtain expression of AGO in wheat or barley to provide resistance to Ggt. One skilled in the art will know of many such plant part-specific promoters which would be useful in the present invention.

Alternatively, the promoters utilized in the double-stranded DNA molecules may be selected to confer specific expression of AGO in response to fungal infection. The infection of plants by fungal pathogens triggers the induction of a wide array of proteins, termed defense-related or pathogenesis-related (PR) proteins [Bowles; Bol et al.; Linthorst]. Such defense-related or PR genes may encode phenylpropanoid metabolism enzymes (such as phenylalanine ammonia lyase, chalcone synthase, 4-coumarate coA ligase, coumaric acid 4-hydroxylase), proteins that modify plant cell walls (such as hydroxyproline-rich glycoproteins, glycine-rich proteins, peroxidases), enzymes (such as chitinases and glucanases) that degrade the fungal cell wall, thaumatin-like proteins, or proteins of as yet unknown function. The defense-related or PR genes have been isolated and characterized from a number of plant species. The promoters of these genes may be used to attain expression of AGO in transgenic plants when challenged with a pathogen, particularly a fungal pathogen such as Pi. Such promoters may derive from defense-related or PR genes isolated from potato itself [Fritzemeier et al.; Cuypers et al.; Logemann et al.; Matton and Brisson; Taylor et al.; Matton et al.; Schroder et al.]. In order to place the AGO gene under the control of a promoter induced by infection with *P. infestans* the promoter reported by Taylor et al. (1990) may be preferred.

The particular promoter selected should be capable of causing sufficient expression of the enzyme coding sequence to result in the production of an effective amount of AGO.

The promoters used in the DNA constructs (i.e. chimeric plant genes) of the present invention may be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al.

An enhanced CaMV 35S promoter has been constructed as follows. A fragment of the CaMV 35S promoter extending between position −343 and +9 was previously constructed in pUC13. [Odell et al.] This segment contains a region identified as being necessary for maximal expression of the CaMV 35S promoter. It was excised as a ClaI-HindIII fragment, made blunt ended with DNA polymerase I (ClaI fragment) and inserted into the HincII site of pUC18. This upstream region of the 35S promoter was excised from this plasmid as a HindIII-EcoRV fragment (extending from −343 to −90) and inserted into the same plasmid between the HindIII and PstI sites. The enhanced CaMV 35S promoter (hereafter "CaMV E35S") thus contains a duplication of sequences between −343 and −90. [Kay et al.]

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs wherein the non-translated region is derived from the 5' non-translated sequence that accompanies the promoter sequence. Rather, the non-translated leader sequence can be derived from an unrelated promoter or coding sequence. For example, the petunia heat shock protein 70 (Hsp70) contains such a leader. [Winter]

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene and (2) plant genes like the soybean 7s storage protein genes and the pea ssRUBISCO E9 gene. [Fischhoff, et al.]

Plant Transformation and Expression

A chimeric plant gene containing a structural coding sequence of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1983), Klee (1985) and EPO publication 0 120 516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

Plants which may be protected by the present invention include, but are not limited to, potatoes, tomatoes, wheat, corn, strawberries, grapes, as well as various ornamentals. Methods of tissue culture and plant regeneration are available for all of these types of plants.

Transient Expression of Glucose Oxidase in Tobacco Plants

A particularly useful plasmid cassette vector for transformation of dicotyledonous plants is pMON999. The expression cassette pMON999 consists of the CaMV E35S promoter, and the 3' end including polyadenylation signals from the NOS gene. pMON999 includes BglII, KpnI and EcoRI sites for insertion of coding sequences and NotI-NotI sites flanking the plant gene expression cassette.

The BglII/KpnI fragment of pMON22514 containing the AGO coding region was inserted into pMON999 to create pMON22515. pMON22515 was electroporated into tobacco protoplasts. Expression of glucose oxidase by the transformed tobacco cells was confirmed by Western blot analysis as well as enzymatic assays.

Stable Transformation of Dicots

The shuttle vector for AGO was created by excising the AGO coding region as a BamHI/BglII fragment from pMON22515. It was then placed in a pUC-based vector, and the resulting plasmid, pMON22579, contains the FMV promoter, the AGO coding region, and the 3' end including polyadenylation signals from the NOS gene. The NotI/NotI fragment from this vector containing the FMV promoter, the AGO coding region, and the NOS gene 3' end including the polyadenylation signal was moved into the NotI restriction site of pMON17227 (WO 92/0449, Barry et al.) to generate the final Ti vector, pMON22587.

As discussed above, an AGO gene can also be expressed in specific parts of a plant by using tissue-specific promoters. The patatin promoter expresses primarily in the tuber of the potato. A KpnI/XbaI fragment containing the AGO coding region was excised from pMON22514 and inserted into a pUC-based vector containing the patatin 1.0 promoter (Bevan et al., 1986) and the 3' end including polyadenylation signals from the NOS gene to create pMON22516. The NotI fragment of pMON-22516 containing the patatin promoter, the AGO coding region and the NOS gene 3' end including the polyadenylation signal was then moved into the NotI restriction site of pMON17227, which was described above, to create the Ti plasmid vector, pMON22517.

These vectors may be introduced into disarmed Agrobacterium ABI and used to transform potato, tomato, or other explants in tissue culture. After selection for kanamycin or glyphosate resistance and plant regeneration, whole plants containing an AGO gene may be recovered. Expression of the glucose oxidase gene may be confirmed by Western blot analysis, enzyme assay, or bioassay.

Expression of AGO by Transformed Potato Plants

Protein was extracted from the tubers of potato plants which had been transformed with the Ti plasmid vector pMON22517 and were examined for the presence of glucose oxidase by Western blot analysis. High levels of glucose oxidase expression were detected in some of the plants. These levels of expression were confirmed by enzymatic assay using the 4-amino antipyrine system. Total protein was extracted from several of these tubers by grinding in 25 mM Phosphate buffer pH7.0+5 mM EDTA+100 mM KCl. Protein was concentrated and washed with 12.5 mM Phosphate Buffer pH7.0.

The protein extracted from tubers expressing AGO was tested against *P. infestans* in the 96-well plate assay in 12.5 mM Phosphate Buffer pH7.0. The results are shown in Table 1. At the highest level of protein tested, 21.2 µg/µl, Pi spores either remained ungerminated or growth from the spores was severely stunted when compared to the Hollow Vector (pMON17227) or Buffer control plant extracts.

TABLE 1

| Treatment | Fungal Inhibition* |
|---|---|
| Buffer control | 0 |
| Hollow vector control | 2 |
| pMON22517, line 9 | 3 |
| pMON22517, line 30 | 3 |

*Scale: 0 = no inhibition, 1 = slight inhibition, 2 = moderate inhibition, 3 = severe inhibition.

Leaves of potato plants transformed with the Ti plasmid vector pMON22587 were tested for the presence of AGO by means of an enzymatic assay. The results are given in Table 2. As above, pMON17227-transformed potato plants were used as hollow vector control plants.

TABLE 2

| Line # | Expression level[a] (%) | Glucose oxidase activity[b] (U/10 ng X $10^{-4}$) | Equivalent to[c] (U/gFW) |
|---|---|---|---|
| Rus. Bur. | 0 | 0 | 0 |
| 22587-2 | 0.075 | 72.2 | 7.22 |
| 22587-3 | 0.150 | 126.4 | 12.64 |
| 22587-4 | 0.007 | 6.0 | 0.6 |
| 22587-12 | 0.125 | 88.2 | 8.82 |
| 22587-31 | 0.350 | 140.4 | 14.04 |
| 22587-32 | 0.350 | 121.0 | 12.10 |

TABLE 2-continued

| Line # | Expression level[a] (%) | Glucose oxidase activity[b] (U/10 ng X $10^{-4}$) | Equivalent to[c] (U/gFW) |
|---|---|---|---|
| 22587-33 | 0.450 | 181.8 | 18.18 |
| 22587-34 | 0.003 | 1.2 | 0.12 |

[a]Expression level is indicated as the percentage of glucose oxidase in total extractable leaf protein.
[b]Glucose oxidase activity in leaf extracts were determined by enzyme activity assay and calculated as units of the enzyme activity in total protein.
[c]Units of glucose oxidase activity per gram fresh weight of leaf tissue (U/gFW) were calculated from the activity in total protein by the conversion factor of 10 μg total protein per gram fresh weight of leaf tissue.

The leaves of potato plants transformed with the Ti plasmid vector pMON22587 were also tested for levels of $H_2O_2$ by titanium chloride precipitation. In two lines the leaves were found to have levels of $H_2O_2$ two- to four-fold higher than the leaves of nontransformed control plant.

Disease-Resistant Potatoes

Tubers expressing AGO were tested against *Erwinia carotovora* in a tuber disc assay. Tubers from 34 lines transformed with pMON22517 were tested for resistance to soft rot lesions. The lines were also tested for expression levels by Western blot analysis. The tubers were surface sterilized according to the method of Yang et al. (1989). Two or three tubers per line were aseptically cut into discs 7–10 mm thick, resulting in six to twelve discs per line. The discs were placed on moistened sterile Whatman #1 filter paper in petri dishes. The center of each disc was inoculated with 50,000 CFU of bacterial in 10 μl. The dishes were maintained in a high humidity environment for 3 days at 23° C. Disease evaluations included measuring the length, radius, and depth of the resulting lesions. Dilutions of macerated tissue from within the lesion were used to determine the final number of bacteria per lesion. The results of this determination are presented in Table 3. For the lines that appeared to be the most protected, all of the measured parameters were better than those of the Hollow Vector and Buffer control tubers. Tubers found to be expressing AGO at the highest level generally had the lowest level of bacteria in the lesions.

TABLE 3

| LINE # | Expression[b] Levels | CFU X $10^9$ |
|---|---|---|
| Buffer Control | null | 16.76 |
| Hollow vector | null | 14.32 |
| 22517-10 | null | 20.7 |
| 22517-24 | null | 20.09 |
| 22517-13 | null | 16.3 |
| 22517-12 | null | 19.26 |
| 22517-9 | LOW | 9.34 |
| 22517-28 | LOW | 13.56 |
| 22517-33 | LOW | 9.57 |
| 22517-14 | LOW | 8.22 |
| 22517-17 | LOW | 8.36 |
| 22517-19 | LOW | 9.37 |
| 22517-32 | LOW | 7.17 |
| 22517-20 | LOW | 7.4 |
| 22517-21 | LOW | 6.25 |
| 22517-34 | LOW | 4.44 |
| 22517-11 | LOW | 3.06 |
| 22517-8 | LOW | 1.5 |
| 22517-7 | MEDIUM | 12.88 |
| 22517-31 | MEDIUM | 12.06 |
| 22517-1 | MEDIUM | 7.54 |
| 22517-15 | MEDIUM | 6.7 |
| 22517-25 | MEDIUM | 12.25 |
| 22517-35 | MEDIUM | 6.81 |

TABLE 3-continued

| LINE # | Expression[b] Levels | CFU X $10^9$ |
|---|---|---|
| 22517-2 | MEDIUM | 3.52 |
| 22517-3 | MEDIUM | 1.26 |
| 22517-5 | MEDIUM | 1.4 |
| 22517-6 | HIGH | 15.74 |
| 22517-18 | HIGH | 2.675 |
| 22517-26 | HIGH | 4.55 |
| 22517-29 | HIGH | 4.35 |
| 22517-4 | HIGH | 4.2 |
| 22517-30 | HIGH | 3.92 |
| 22517-16 | HIGH | 1.12 |
| 22517-23 | HIGH | 2.67 |
| 22517-36 | HIGH | 0.855 |

[a]CFU = colony forming units
[b]Expression levels determined by Western Blot Analysis Leaflets from plants transformed with pMON22587 and expressing AGO were tested for resistance to Pi. Fully expanded leaflets (~20 cm$^2$) were inoculated by adding droplets of 100 μl sporangium suspension of *Phytophthora infestans* to the center of the abaxial leaf surface. The inocula had a density of $10^5$–$10^6$ sporangia per ml collected from 2–3 week old plates containing LB-V8 medium. The inoculated leaflets were maintained in Nunc Bio-Assay dishes (243×243×18 cm) with moisture provided by wet filter paper at the bottom, and incubated in growth chambers at ~19° C. with 16 h photoperiod. The development of symptoms was observed and infected areas on the leaflets were measured by overlaying each leaflet with a 5 mm×5 mm transparent grid. For each line of leaflets, the mean of infected areas and the standard deviation were calculated.

The transgenic lines expressing AGO showed significant control of the symptoms caused by *Phytophthora infestans* infection on the leaflets. The results of two lines are shown in Table 4. The symptom reduction was 47 and 57% as compared to controls (both nontransformed and hollow vector transformants).

TABLE 4

| | Area of Infection[a](cm$^2$) | | | |
|---|---|---|---|---|
| Line No. | 3 dpi[b] | 4 dpi | 5 dpi | 6 dpi |
| Russet Burbank | 1.2 | 2.1 | 4.2 | 7.1 |
| 17227-1[c] | 1.6 | 2.7 | 4.7 | 8.7 |
| 22587-3[d] | 0.4 | 0.8 | 1.1 | 3.0 |
| 22587-12[d] | 0.5 | 1.3 | 2.3 | 3.7 |

[a]Area of infection is indicated as the mean of five leaflets.
[b]Days post inoculation.
[c]A control line transformed with vector only.
[d]Transgenic lines expressing glucose oiddase.

Stable Transformation of Monocots

For transformation of monocots a vector was constructed with AGO and an intron particularly useful in increasing frequency of obtaining transformed plants which express a desired protein at high levels. The hsp70 intron disclosed in EP 602 193 (equivalent to U.S. Ser. No. 08/181,364, Brown et al., incorporated herein by reference) was used. pMON19477, disclosed therein, was cut, and the 800 bp BglII-BamHI fragment containing the hsp70 intron was then cloned into the unique BglII site in pMON22515, resulting in pMON22623.

pMON22623 has been introduced into wheat cells by microprojectile bombardment. Immature wheat embryos were isolated as described by Vasil et al. Embryogenic callus was obtained by culturing the immature embryos for 4 to 7 days, on a modified MS medium comprising about 40 g/l maltose and about 2 mg/l 2,4-D. The callus was subjected to bombardment with microprojectiles coated with pMON22623 and a plasmid containing a bialophos resistance gene. One day after bombardment the immature embryos were transferred to a growth medium containing the selective agent bialaphos. After seven days on the growth and selective medium the immature embryo-derived callus was removed to a shoot-producing medium (modified MS medium no 2,4-D) containing bialophos and grown for 28–40 days. A PCR assay will be done to confirm that the glucose oxidase gene is present in the shoots. Shoots containing the glucose oxidase gene will be rooted and taken to soil. When transformed plants are recovered, their fungal resistance capacity, particularly to Ggt, will be assessed by known methods.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

REFERENCES

Barry, G. F., G. Kishore, and S. R. Padgette. "Glyphosate Tolerant 5-Enolpyruvylshikimate- 3-phosphate Synthases." PCT Appl. WO 92/04449, 1991.
Bevan, M. et al. *Nature*, 304:184, 1983.
Bevan, M. et al. *Nucleic Acid Research*, 14:4625, 1986.
Bol, J. et al. *Ann Rev of Phytopathol.*, 28:113–138, 1990.
Bowles, D. *Ann Rev of Biochem.*, 59:873–907, 1990.
Cuypers, B. et al. *Mol Plant-Microbe Interactions*, 1:157–160, 1988.
Fischhoff, D. A. and Perlak, F. J. "Synthetic plant genes and method for preparation." European Patent Application, Publication Number 0 385 962, 1990.
Frederick, K. et al. *J. Biol. Chem.*, 265:3793–3802.
Fritzemeier, K. et al. *Plant Physiol.*, 85:34–41, 1987.
Gallo. *Methods in Enzymology*, 71:665–668, 1981.
Herrera-Estrella, L. et al. *Nature*, 303:20–9, 1983.
Kay, R. et al., *Science*, 236:1299–1302, 1987.
Keil, M. et al. *Nucleic Acids Res.*, 14:5641–5650, 1986.
Klee, H. J. et al. *Bio/Technology*, 3:637–642, 1985.
Kim, K. et al. *Phytopathology*, 78:488–492, 1988.
Kim, K. et al. *Can. J. Microbiol.*, 36:199–205, 1990.
Kriechbaum M. et al. *FEBS Lett.*, 255:63–66, 1989.
Linthorst, H. J. M. *Crit Rev Plant Sci*, 10:123–150.
Logemann, J. et al. *Plant Cell*, 1:151–158, 1989.
Matton, D. and Brisson, N. *Mol Plant-Microbe Interactions*, 2:325–331, 1989.
Matton, D. et al. *Plant Mol Biol*, 14:863–865, 1990.
Nelson, C. et al. *Proc. Natl. Acad. Sci. USA*, 77:1975–1979, 1980.
Odell, J. et al., *Nature*, 313:810, 1985.
Schroder, M. et al. *Plant J.*, 2:161–172, 1992.
Taylor, J., et al. *Molecular Plant-Microbe Interactions*, 3:72–77, 1990.
Vasil et al. *Bio/Technology* 11:1153–1158, 1993.
Winter et al. *Mol. Gen. Genet.*, 221(2):315–19, 1988.

What is claimed is:

1. A recombinant, double-stranded DNA molecule comprising in operative sequence:
    a) a promoter which functions in plant cells to cause the production of an RNA sequence;
    b) a structural coding sequence that encodes for production of Aspergillus glucose oxidase; and
    c) a 3' non-translated region which functions in plant cells to cause the addition of polyadenylate nucleotides to the 3' end of the RNA sequence.

2. The DNA molecule of claim 1 wherein said structural DNA sequence is SEQ ID NO:1.

3. The DNA molecule of claim 1 wherein said promoter is selected from FMV35S and CaMV35S promoters.

4. The DNA molecule of claim 1 wherein said promoter is induced by a pathogenic infection.

5. A method of producing genetically transformed, disease resistant plants, comprising the steps of:
    a) inserting into the genome of a plant cell a recombinant, double-stranded DNA molecule comprising
        (i) a promoter which functions in plant cells to cause the production of an RNA sequence;
        (ii) a structural coding sequence that causes the production of Aspergillus glucose oxidase;
        (iii) a 3' non-translated region which functions in said plant cells to cause the addition of polyadenylate nucleotides to the 3' end of the RNA sequence;
    b) obtaining transformed plant cells; and
    c) regenerating from the transformed plant cells genetically transformed plants which express Aspergillus glucose oxidase in an amount effective to reduce damage due to infection by a bacterial or fungal pathogen.

6. The method of claim 5 wherein said structural coding sequence is SEQ ID NO:1.

7. The method of claim 5 wherein said promoter is selected from FMV35S and CaMV35S promoters.

8. The method of claim 5 wherein said promoter is induced by pathogen infection.

9. A genetically transformed, disease resistant plant comprising a recombinant, double-stranded DNA molecule comprising in operative sequence:
    a) a promoter which functions in plant cells to cause the production of an RNA sequence;
    b) a structural coding sequence that encodes for production of Aspergillus glucose oxidase; and
    c) a 3' non-translated region which functions in plant cells to cause the addition of polyadenylate nucleotides to the 3' end of the RNA sequence.

10. The plant of claim 9 wherein said promoter is selected from FMV35S and CaMV35S promoters.

11. The plant of claim 9 wherein said promoter is induced by pathogen infection.

12. The plant of claim 9 wherein said structural coding sequence is SEQ ID NO:1.

13. The plant of claim 12 which is a potato plant.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1848 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 16..1833

( x i ) SEQUENCE DESCRIPTION: SEQ ID NO:1:

```
TCTAGAAGAT CTATC ATG CAG ACT CTC CTT GTG AGC TCG CTT GTG GTC TCC          51
                 Met Gln Thr Leu Leu Val Ser Ser Leu Val Val Ser
                  1               5                      10

CTC GCT GCG GCC CTG CCA CAC TAC ATC AGG AGC AAT GGC ATT GAA GCC           99
Leu Ala Ala Ala Leu Pro His Tyr Ile Arg Ser Asn Gly Ile Glu Ala
         15                  20                  25

AGC CTC CTG ACT GAT CCC AAG GAT GTC TCC GGC CGC ACG GTC GAC TAC          147
Ser Leu Leu Thr Asp Pro Lys Asp Val Ser Gly Arg Thr Val Asp Tyr
     30                  35                  40

ATC ATC GCT GGT GGA GGT CTG ACT GGA CTC ACC ACC GCT GCT CGT CTG          195
Ile Ile Ala Gly Gly Gly Leu Thr Gly Leu Thr Thr Ala Ala Arg Leu
 45                  50                  55                  60

ACG GAG AAC CCC AAC ATC AGT GTG CTC GTC ATC GAA AGT GGC TCC TAC          243
Thr Glu Asn Pro Asn Ile Ser Val Leu Val Ile Glu Ser Gly Ser Tyr
                 65                  70                  75

GAG TCG GAC AGA GGT CCT ATC ATT GAG GAC CTG AAC GCC TAC GGC GAC          291
Glu Ser Asp Arg Gly Pro Ile Ile Glu Asp Leu Asn Ala Tyr Gly Asp
             80                  85                  90

ATC TTT GGC AGC AGT GTA GAC CAC GCC TAC GAG ACC GTG GAG CTC GCT          339
Ile Phe Gly Ser Ser Val Asp His Ala Tyr Glu Thr Val Glu Leu Ala
         95                 100                 105

ACC AAC AAT CAA ACC GCG CTG ATC CGC TCC GGA AAT GGT CTC GGT GGC          387
Thr Asn Asn Gln Thr Ala Leu Ile Arg Ser Gly Asn Gly Leu Gly Gly
     110                 115                 120

TCT ACT CTA GTG AAT GGT GGC ACC TGG ACT CGC CCC CAC AAG GCA CAG          435
Ser Thr Leu Val Asn Gly Gly Thr Trp Thr Arg Pro His Lys Ala Gln
125                 130                 135                 140

GTT GAC TCT TGG GAG ACT GTC TTT GGA AAT GAG GGC TGG AAC TGG GAC          483
Val Asp Ser Trp Glu Thr Val Phe Gly Asn Glu Gly Trp Asn Trp Asp
                 145                 150                 155

AAT GTG GCC GCC TAC TCC CTC CAG GCT GAG CGT GCT CGC GCA CCA AAT          531
Asn Val Ala Ala Tyr Ser Leu Gln Ala Glu Arg Ala Arg Ala Pro Asn
             160                 165                 170

GCC AAA CAG ATC GCT GCT GGC CAC TAC TTC AAC GCA TCC TGC CAT GGT          579
Ala Lys Gln Ile Ala Ala Gly His Tyr Phe Asn Ala Ser Cys His Gly
         175                 180                 185

GTT AAT GGT ACT GTC CAT GCC GGA CCC CGC GAC ACC GGC GAT GAC TAT          627
Val Asn Gly Thr Val His Ala Gly Pro Arg Asp Thr Gly Asp Asp Tyr
     190                 195                 200

TCT CCC ATC GTC AAG GCT CTC ATG AGC GCT GTC GAA GAC CGG GGC GTT          675
Ser Pro Ile Val Lys Ala Leu Met Ser Ala Val Glu Asp Arg Gly Val
205                 210                 215                 220
```

| | | | | | | | | | | | | | | | | |
|---|---|---|---|---|---|---|---|---|---|---|---|---|---|---|---|---|
| CCC | ACC | AAG | AAA | GAC | TTC | GGA | TGC | GGT | GAC | CCC | CAT | GGT | GTG | TCC | ATG | 723 |
| Pro | Thr | Lys | Lys<br>225 | Asp | Phe | Gly | Cys | Gly<br>230 | Asp | Pro | His | Gly | Val | Ser<br>235 | Met | |
| TTC | CCC | AAC | ACC | TTG | CAC | GAA | GAC | CAA | GTG | CGC | TCC | GAT | GCC | GCT | CGC | 771 |
| Phe | Pro | Asn | Thr<br>240 | Leu | His | Glu | Asp | Gln<br>245 | Val | Arg | Ser | Asp | Ala<br>250 | Ala | Arg | |
| GAA | TGG | CTA | CTT | CCC | AAC | TAC | CAA | CGT | CCC | AAC | CTG | CAA | GTC | CTG | ACC | 819 |
| Glu | Trp | Leu<br>255 | Leu | Pro | Asn | Tyr | Gln<br>260 | Arg | Pro | Asn | Leu | Gln<br>265 | Val | Leu | Thr | |
| GGA | CAG | TAT | GTT | GGT | AAG | GTG | CTC | CTT | AGC | CAG | AAC | GGC | ACC | ACC | CCT | 867 |
| Gly | Gln<br>270 | Tyr | Val | Gly | Lys<br>275 | Val | Leu | Leu | Ser | Gln<br>280 | Asn | Gly | Thr | Thr | Pro | |
| CGT | GCC | GTT | GGC | GTG | GAA | TTC | GGC | ACC | CAC | AAG | GGC | AAC | ACC | CAC | AAC | 915 |
| Arg<br>285 | Ala | Val | Gly | Val | Glu<br>290 | Phe | Gly | Thr | His | Lys<br>295 | Gly | Asn | Thr | His | Asn<br>300 | |
| GTT | TAC | GCT | AAG | CAC | GAG | GTC | CTC | CTG | GCC | GCG | GGC | TCC | GCT | GTC | TCT | 963 |
| Val | Tyr | Ala | Lys | His<br>305 | Glu | Val | Leu | Leu | Ala<br>310 | Ala | Gly | Ser | Ala | Val<br>315 | Ser | |
| CCC | ACA | ATC | CTC | GAA | TAT | TCC | GGT | ATC | GGA | ATG | AAG | TCC | ATC | CTG | GAG | 1011 |
| Pro | Thr | Ile | Leu<br>320 | Glu | Tyr | Ser | Gly | Ile<br>325 | Gly | Met | Lys | Ser | Ile<br>330 | Leu | Glu | |
| CCC | CTT | GGT | ATC | GAC | ACC | GTC | GTT | GAC | CTG | CCC | GTC | GGC | TTG | AAC | CTG | 1059 |
| Pro | Leu | Gly<br>335 | Ile | Asp | Thr | Val | Val<br>340 | Asp | Leu | Pro | Val | Gly<br>345 | Leu | Asn | Leu | |
| CAG | GAC | CAG | ACC | ACC | GCT | ACC | GTC | CGC | TCC | CGC | ATC | ACC | TCT | GCT | GGT | 1107 |
| Gln | Asp<br>350 | Gln | Thr | Thr | Ala | Thr<br>355 | Val | Arg | Ser | Arg | Ile<br>360 | Thr | Ser | Ala | Gly | |
| GCA | GGA | CAG | GGA | CAG | GCC | GCT | TGG | TTC | GCC | ACC | TTC | AAC | GAG | ACC | TTT | 1155 |
| Ala<br>365 | Gly | Gln | Gly | Gln<br>370 | Ala | Ala | Trp | Phe | Ala<br>375 | Thr | Phe | Asn | Glu | Thr<br>380 | Phe | |
| GGT | GAC | TAT | TCC | GAA | AAG | GCA | CAC | GAG | CTG | CTC | AAC | ACC | AAG | CTG | GAG | 1203 |
| Gly | Asp | Tyr | Ser | Glu<br>385 | Lys | Ala | His | Glu | Leu<br>390 | Leu | Asn | Thr | Lys | Leu<br>395 | Glu | |
| CAG | TGG | GCC | GAA | GAG | GCC | GTC | GCC | CGT | GGC | GGA | TTC | CAC | AAC | ACC | ACC | 1251 |
| Gln | Trp | Ala | Glu<br>400 | Glu | Ala | Val | Ala | Arg<br>405 | Gly | Gly | Phe | His | Asn<br>410 | Thr | Thr | |
| GCC | TTG | CTC | ATC | CAG | TAC | GAG | AAC | TAC | CGC | GAC | TGG | ATT | GTC | AAC | CAC | 1299 |
| Ala | Leu | Leu<br>415 | Ile | Gln | Tyr | Glu | Asn<br>420 | Tyr | Arg | Asp | Trp | Ile<br>425 | Val | Asn | His | |
| AAC | GTC | GCG | TAC | TCG | GAA | CTC | TTC | CTC | GAC | ACT | GCC | GGA | GTA | GCC | AGC | 1347 |
| Asn | Val<br>430 | Ala | Tyr | Ser | Glu | Leu<br>435 | Phe | Leu | Asp | Thr | Ala<br>440 | Gly | Val | Ala | Ser | |
| TTC | GAT | GTG | TGG | GAC | CTT | CTG | CCC | TTC | ACC | CGA | GGA | TAC | GTT | CAC | ATC | 1395 |
| Phe | Asp<br>445 | Val | Trp | Asp | Leu | Leu<br>450 | Pro | Phe | Thr | Arg | Gly<br>455 | Tyr | Val | His | Ile<br>460 | |
| CTC | GAC | AAG | GAC | CCC | TAC | CTT | CAC | CAC | TTC | GCC | TAC | GAC | CCT | CAG | TAC | 1443 |
| Leu | Asp | Lys | Asp | Pro<br>465 | Tyr | Leu | His | His | Phe<br>470 | Ala | Tyr | Asp | Pro | Gln<br>475 | Tyr | |
| TTC | CTC | AAC | GAG | CTG | GAC | CTG | CTC | GGT | CAG | GCT | GCC | GCT | ACT | CAA | CTG | 1491 |
| Phe | Leu | Asn | Glu<br>480 | Leu | Asp | Leu | Leu | Gly<br>485 | Gln | Ala | Ala | Ala | Thr<br>490 | Gln | Leu | |
| GCC | CGC | AAC | ATC | TCC | AAC | TCC | GGT | GCC | ATG | CAG | ACC | TAC | TTC | GCT | GGG | 1539 |
| Ala | Arg | Asn<br>495 | Ile | Ser | Asn | Ser<br>500 | Gly | Ala | Met | Gln | Thr<br>505 | Tyr | Phe | Ala | Gly | |
| GAG | ACT | ATC | CCC | GGT | GAT | AAC | CTC | GCG | TAT | GAT | GCC | GAT | TTG | AGC | GCC | 1587 |
| Glu | Thr | Ile<br>510 | Pro | Gly | Asp | Asn | Leu<br>515 | Ala | Tyr | Asp | Ala | Asp<br>520 | Leu | Ser | Ala | |
| TGG | ACT | GAG | TAC | ATC | CCG | TAC | CAC | TTC | CGT | CCT | AAC | TAC | CAT | GGC | GTG | 1635 |
| Trp | Thr | Glu<br>525 | Tyr | Ile | Pro<br>530 | Tyr | His | Phe | Arg<br>535 | Pro | Asn | Tyr | His<br>540 | Gly | Val | |

| | | | | | | | | | | | | | | | | |
|---|---|---|---|---|---|---|---|---|---|---|---|---|---|---|---|---|
| GGT | ACT | TGC | TCC | ATG | ATG | CCG | AAG | GAG | ATG | GGC | GGT | GTT | GTT | GAT | AAT | 1683 |
| Gly | Thr | Cys | Ser | Met | Met | Pro | Lys | Glu | Met | Gly | Gly | Val | Val | Asp | Asn | |
| | | | | 545 | | | | 550 | | | | | 555 | | | |
| GCT | GCC | CGT | GTG | TAT | GGT | GTG | CAG | GGA | CTG | CGT | GTC | ATT | GAT | GGT | TCT | 1731 |
| Ala | Ala | Arg | Val | Tyr | Gly | Val | Gln | Gly | Leu | Arg | Val | Ile | Asp | Gly | Ser | |
| | | | 560 | | | | | 565 | | | | | 570 | | | |
| ATT | CCT | CCT | ACG | CAA | ATG | TCG | TCC | CAT | GTC | ATG | ACG | GTG | TTC | TAT | GCC | 1779 |
| Ile | Pro | Pro | Thr | Gln | Met | Ser | Ser | His | Val | Met | Thr | Val | Phe | Tyr | Ala | |
| | | 575 | | | | | 580 | | | | | 585 | | | | |
| ATG | GCG | CTA | AAA | ATT | TCG | GAT | GCT | ATC | TTG | GAA | GAT | TAT | GCT | TCC | ATG | 1827 |
| Met | Ala | Leu | Lys | Ile | Ser | Asp | Ala | Ile | Leu | Glu | Asp | Tyr | Ala | Ser | Met | |
| | 590 | | | | | 595 | | | | | 600 | | | | | |
| CAG | TGATAAGGAT | CCGGTACC | | | | | | | | | | | | | | 1848 |
| Gln | | | | | | | | | | | | | | | | |
| 605 | | | | | | | | | | | | | | | | |

( 2 ) INFORMATION FOR SEQ ID NO:2:

( i ) SEQUENCE CHARACTERISTICS:
( A ) LENGTH: 605 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Gln | Thr | Leu | Leu | Val | Ser | Ser | Leu | Val | Ser | Leu | Ala | Ala | Ala |
| 1 | | | | 5 | | | | | 10 | | | | | 15 |
| Leu | Pro | His | Tyr | Ile | Arg | Ser | Asn | Gly | Ile | Glu | Ala | Ser | Leu | Leu | Thr |
| | | | 20 | | | | | 25 | | | | | 30 | | |
| Asp | Pro | Lys | Asp | Val | Ser | Gly | Arg | Thr | Val | Asp | Tyr | Ile | Ile | Ala | Gly |
| | | 35 | | | | | 40 | | | | | 45 | | | |
| Gly | Gly | Leu | Thr | Gly | Leu | Thr | Thr | Ala | Ala | Arg | Leu | Thr | Glu | Asn | Pro |
| | 50 | | | | | 55 | | | | | 60 | | | | |
| Asn | Ile | Ser | Val | Leu | Val | Ile | Glu | Ser | Gly | Ser | Tyr | Glu | Ser | Asp | Arg |
| 65 | | | | | 70 | | | | | 75 | | | | | 80 |
| Gly | Pro | Ile | Ile | Glu | Asp | Leu | Asn | Ala | Tyr | Gly | Asp | Ile | Phe | Gly | Ser |
| | | | | 85 | | | | | 90 | | | | | 95 | |
| Ser | Val | Asp | His | Ala | Tyr | Glu | Thr | Val | Glu | Leu | Ala | Thr | Asn | Asn | Gln |
| | | | 100 | | | | | 105 | | | | | 110 | | |
| Thr | Ala | Leu | Ile | Arg | Ser | Gly | Asn | Gly | Leu | Gly | Gly | Ser | Thr | Leu | Val |
| | | 115 | | | | | 120 | | | | | 125 | | | |
| Asn | Gly | Gly | Thr | Trp | Thr | Arg | Pro | His | Lys | Ala | Gln | Val | Asp | Ser | Trp |
| | 130 | | | | | 135 | | | | | 140 | | | | |
| Glu | Thr | Val | Phe | Gly | Asn | Glu | Gly | Trp | Asn | Trp | Asp | Asn | Val | Ala | Ala |
| 145 | | | | | 150 | | | | | 155 | | | | | 160 |
| Tyr | Ser | Leu | Gln | Ala | Glu | Arg | Ala | Arg | Ala | Pro | Asn | Ala | Lys | Gln | Ile |
| | | | | 165 | | | | | 170 | | | | | 175 | |
| Ala | Ala | Gly | His | Tyr | Phe | Asn | Ala | Ser | Cys | His | Gly | Val | Asn | Gly | Thr |
| | | | 180 | | | | | 185 | | | | | 190 | | |
| Val | His | Ala | Gly | Pro | Arg | Asp | Thr | Gly | Asp | Asp | Tyr | Ser | Pro | Ile | Val |
| | | 195 | | | | | 200 | | | | | 205 | | | |
| Lys | Ala | Leu | Met | Ser | Ala | Val | Glu | Asp | Arg | Gly | Val | Pro | Thr | Lys | Lys |
| | 210 | | | | | 215 | | | | | 220 | | | | |
| Asp | Phe | Gly | Cys | Gly | Asp | Pro | His | Gly | Val | Ser | Met | Phe | Pro | Asn | Thr |
| 225 | | | | | 230 | | | | | 235 | | | | | 240 |
| Leu | His | Glu | Asp | Gln | Val | Arg | Ser | Asp | Ala | Ala | Arg | Glu | Trp | Leu | Leu |
| | | | | 245 | | | | | 250 | | | | | 255 | |

| Pro | Asn | Tyr | Gln | Arg | Pro | Asn | Leu | Gln | Val | Leu | Thr | Gly | Gln | Tyr | Val |
|---|---|---|---|---|---|---|---|---|---|---|---|---|---|---|---|
| | | | 260 | | | | 265 | | | | | 270 | | | |
| Gly | Lys | Val | Leu | Leu | Ser | Gln | Asn | Gly | Thr | Thr | Pro | Arg | Ala | Val | Gly |
| | | 275 | | | | 280 | | | | | 285 | | | | |
| Val | Glu | Phe | Gly | Thr | His | Lys | Gly | Asn | Thr | His | Asn | Val | Tyr | Ala | Lys |
| | 290 | | | | 295 | | | | | 300 | | | | | |
| His | Glu | Val | Leu | Leu | Ala | Ala | Gly | Ser | Ala | Val | Ser | Pro | Thr | Ile | Leu |
| 305 | | | | 310 | | | | 315 | | | | | | | 320 |
| Glu | Tyr | Ser | Gly | Ile | Gly | Met | Lys | Ser | Ile | Leu | Glu | Pro | Leu | Gly | Ile |
| | | | 325 | | | | | 330 | | | | | 335 | | |
| Asp | Thr | Val | Val | Asp | Leu | Pro | Val | Gly | Leu | Asn | Leu | Gln | Asp | Gln | Thr |
| | | | 340 | | | | 345 | | | | 350 | | | | |
| Thr | Ala | Thr | Val | Arg | Ser | Arg | Ile | Thr | Ser | Ala | Gly | Ala | Gly | Gln | Gly |
| | | 355 | | | | 360 | | | | 365 | | | | | |
| Gln | Ala | Ala | Trp | Phe | Ala | Thr | Phe | Asn | Glu | Thr | Phe | Gly | Asp | Tyr | Ser |
| | 370 | | | | 375 | | | | 380 | | | | | | |
| Glu | Lys | Ala | His | Glu | Leu | Leu | Asn | Thr | Lys | Leu | Glu | Gln | Trp | Ala | Glu |
| 385 | | | | 390 | | | | 395 | | | | | | | 400 |
| Glu | Ala | Val | Ala | Arg | Gly | Gly | Phe | His | Asn | Thr | Thr | Ala | Leu | Leu | Ile |
| | | | 405 | | | | 410 | | | | | 415 | | | |
| Gln | Tyr | Glu | Asn | Tyr | Arg | Asp | Trp | Ile | Val | Asn | His | Asn | Val | Ala | Tyr |
| | | | 420 | | | | 425 | | | | | 430 | | | |
| Ser | Glu | Leu | Phe | Leu | Asp | Thr | Ala | Gly | Val | Ala | Ser | Phe | Asp | Val | Trp |
| | | 435 | | | | 440 | | | | 445 | | | | | |
| Asp | Leu | Leu | Pro | Phe | Thr | Arg | Gly | Tyr | Val | His | Ile | Leu | Asp | Lys | Asp |
| | 450 | | | | 455 | | | | 460 | | | | | | |
| Pro | Tyr | Leu | His | His | Phe | Ala | Tyr | Asp | Pro | Gln | Tyr | Phe | Leu | Asn | Glu |
| 465 | | | | 470 | | | | 475 | | | | | | | 480 |
| Leu | Asp | Leu | Leu | Gly | Gln | Ala | Ala | Ala | Thr | Gln | Leu | Ala | Arg | Asn | Ile |
| | | | 485 | | | | 490 | | | | | 495 | | | |
| Ser | Asn | Ser | Gly | Ala | Met | Gln | Thr | Tyr | Phe | Ala | Gly | Glu | Thr | Ile | Pro |
| | | | 500 | | | | 505 | | | | | 510 | | | |
| Gly | Asp | Asn | Leu | Ala | Tyr | Asp | Ala | Asp | Leu | Ser | Ala | Trp | Thr | Glu | Tyr |
| | | 515 | | | | 520 | | | | | 525 | | | | |
| Ile | Pro | Tyr | His | Phe | Arg | Pro | Asn | Tyr | His | Gly | Val | Gly | Thr | Cys | Ser |
| | 530 | | | | | 535 | | | | | 540 | | | | |
| Met | Met | Pro | Lys | Glu | Met | Gly | Gly | Val | Val | Asp | Asn | Ala | Ala | Arg | Val |
| 545 | | | | | 550 | | | | | 555 | | | | | 560 |
| Tyr | Gly | Val | Gln | Gly | Leu | Arg | Val | Ile | Asp | Gly | Ser | Ile | Pro | Pro | Thr |
| | | | | 565 | | | | 570 | | | | | 575 | | |
| Gln | Met | Ser | Ser | His | Val | Met | Thr | Val | Phe | Tyr | Ala | Met | Ala | Leu | Lys |
| | | | 580 | | | | 585 | | | | | 590 | | | |
| Ile | Ser | Asp | Ala | Ile | Leu | Glu | Asp | Tyr | Ala | Ser | Met | Gln | | | |
| | | 595 | | | | 600 | | | | | 605 | | | | |

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CCATCTAGAA GATCTATCAT GCAGACTCTC CTT        33

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TGGGGTACCG GATCCTTATC ACTGCATGGA AGCATA      36